United States Patent
Sokolov et al.

(10) Patent No.: US 10,744,160 B2
(45) Date of Patent: Aug. 18, 2020

(54) STEM CELL MATERIAL AND METHOD OF MANUFACTURING

(71) Applicant: T-HELPER CELL TECHNOLOGIES, LLC, Moscow (RU)

(72) Inventors: Anatoliy Sokolov, Moscow (RU); Antonina Ivanovna Kolesnikova, Moscow (RU); Andrei Igorevich Dovgii, Moscow (RU)

(73) Assignee: T-Helper Cell Technologies, LLC, Moscow (RU)

( * ) Notice: Subject to any disclaimer, the term of this patent is extended or adjusted under 35 U.S.C. 154(b) by 0 days.

(21) Appl. No.: 15/531,532

(22) PCT Filed: Nov. 30, 2015

(86) PCT No.: PCT/RU2015/000831
§ 371 (c)(1),
(2) Date: May 30, 2017

(87) PCT Pub. No.: WO2016/089252
PCT Pub. Date: Jun. 9, 2016

(65) Prior Publication Data
US 2017/0326178 A1    Nov. 16, 2017

(30) Foreign Application Priority Data
Dec. 1, 2014  (RU) ................ 2014148251

(51) Int. Cl.
*A61K 35/28* (2015.01)
*C12N 5/0775* (2010.01)
*A61L 27/38* (2006.01)

(52) U.S. Cl.
CPC .......... *A61K 35/28* (2013.01); *A61L 27/3834* (2013.01); *C12N 5/0662* (2013.01); *C12N 5/0663* (2013.01); *C12N 2501/15* (2013.01); *C12N 2501/165* (2013.01); *C12N 2501/21* (2013.01); *C12N 2501/25* (2013.01)

(58) Field of Classification Search
CPC ... A61K 35/28; A61L 27/3834; C12N 5/0662; C12N 5/0663; C12N 2501/15; C12N 2501/165; C12N 2501/21; C12N 2501/25
USPC ...................................... 424/93.7
See application file for complete search history.

(56) References Cited

U.S. PATENT DOCUMENTS

| | | | |
|---|---|---|---|
| 5,486,359 A | 1/1996 | Caplan et al. | |
| 7,704,739 B2 | 4/2010 | Han et al. | |
| 8,287,853 B2 | 10/2012 | Cool et al. | |
| 8,318,197 B2 | 11/2012 | Steed et al. | |
| 8,361,485 B2 | 1/2013 | Naughton et al. | |
| 2002/0085996 A1 | 7/2002 | McIntosh et al. | |
| 2003/0103951 A1 | 6/2003 | Pittenger et al. | |
| 2004/0142861 A1 | 7/2004 | Mansbridge | |
| 2005/0164380 A1 | 7/2005 | Trisler et al. | |
| 2006/0083722 A1 | 4/2006 | Cibelli et al. | |
| 2006/0100124 A1 | 5/2006 | Mostoller | |
| 2007/0067860 A1 | 3/2007 | West et al. | |
| 2007/0243158 A1 | 10/2007 | Ronfard et al. | |
| 2007/0274960 A1 | 11/2007 | Harman et al. | |
| 2008/0206171 A1 | 8/2008 | Gueniche | |
| 2009/0136459 A1 | 5/2009 | Wu et al. | |
| 2009/0137040 A1 | 5/2009 | Cibelli et al. | |
| 2009/0169527 A1 | 7/2009 | Chopp et al. | |
| 2010/0226976 A1 | 9/2010 | Machluf et al. | |
| 2010/0310517 A1 | 12/2010 | Brem et al. | |
| 2010/0323027 A1 | 12/2010 | Lim et al. | |
| 2011/0003008 A1 | 1/2011 | Lim | |
| 2011/0129439 A1* | 6/2011 | Herrera Sanchez | A61K 35/407 424/85.2 |
| 2011/0129447 A1 | 6/2011 | Meretzki et al. | |
| 2011/0177015 A1 | 7/2011 | Friedlander | |
| 2011/0212062 A1 | 9/2011 | Falanga | |
| 2011/0318315 A1 | 12/2011 | Aggarwal et al. | |
| 2012/0058089 A1 | 3/2012 | Hariri | |
| 2012/0107413 A1 | 5/2012 | Lim et al. | |
| 2012/0189585 A1 | 7/2012 | Giampapa et al. | |
| 2012/0207705 A1 | 8/2012 | Kara | |
| 2012/0251489 A1 | 10/2012 | Herrera Sanchez et al. | |

(Continued)

FOREIGN PATENT DOCUMENTS

| | | |
|---|---|---|
| EP | 1 276 486 | 11/2010 |
| EP | 1 773 908 | 9/2012 |

(Continued)

OTHER PUBLICATIONS

Zisa et al., Vascular endothelial growth factor (VEGF) as a key therapeutic trophic factor in bone marrow mesenchymal stem cell-mediated cardiac repair, Biochem Biophys Res Commun, Dec. 18, 2009; 390(3): 834-838.*

Noort et al., Angiogenic factors produced by fetal lung mesenchymal stromal cells, 2011, Chapter 6, p. 174-193, Available online at: research.vu.nl/ws/portalfiles/portal/42210453/ hoofdstuk+Angiogenic+factors+produced+by.pdf.*

Meirelles et al., Mechanisms involved in the therapeutic properties of mesenchymal stem cells, Cytokine & Growth Factor Reviews, 20 (2009) p. 419-427.*

(Continued)

*Primary Examiner* — Jennifer M. H. Tichy
(74) *Attorney, Agent, or Firm* — Wenderoth, Lind & Ponack, L.L.P.

(57) ABSTRACT

Aspects of the invention relate to a novel mesenchymal stem cell line (hb-MSC), a culture medium conditioned by the hb-MSC line, and various hb-MSC compositions. The hb-MSC composition may include a plurality of hb-MSCs, an hb-MSC conditioned medium, or a combination thereof. The hb-MSC composition may also include an appropriate carrier. Also described are methods of use for the hb-MSC cells, the conditioned medium and compositions thereof.

31 Claims, 4 Drawing Sheets

Specification includes a Sequence Listing.

(56) References Cited

U.S. PATENT DOCUMENTS

| | | |
|---|---|---|
| 2012/0263692 A1 | 10/2012 | Bertone |
| 2012/0276215 A1 | 11/2012 | Riordan et al. |
| 2012/0294949 A1 | 11/2012 | Johnstone et al. |
| 2012/0301538 A1 | 11/2012 | Gordon-Beresford et al. |
| 2012/0308535 A1 | 12/2012 | Gambacurta et al. |
| 2013/0039896 A1 | 2/2013 | Smith et al. |
| 2013/0058903 A1 | 3/2013 | Lee |
| 2013/0089514 A1 | 4/2013 | Cohen et al. |
| 2013/0110132 A1 | 5/2013 | Epstein et al. |

FOREIGN PATENT DOCUMENTS

| | | |
|---|---|---|
| JP | 2011-522553 | 8/2011 |
| RU | 2138246 | 9/1999 |
| RU | 2 292 212 | 1/2007 |
| RU | 2007 121 843 | 12/2008 |
| RU | 2341270 | 12/2008 |
| RU | 2372933 | 11/2009 |
| RU | 2432943 | 11/2011 |
| RU | 2512681 | 4/2014 |
| RU | 2 528 250 | 9/2014 |
| WO | 98/32450 | 7/1998 |
| WO | 01/32189 | 5/2001 |
| WO | 2008/060374 | 5/2008 |
| WO | 2008/070868 | 6/2008 |
| WO | 2009/150199 | 12/2009 |
| WO | 2011/042547 | 4/2011 |
| WO | 2011/052818 | 5/2011 |
| WO | 2011/063005 | 5/2011 |
| WO | 2013/132428 | 9/2013 |
| WO | 2014/039429 | 3/2014 |
| WO | 2015/028900 | 3/2015 |

OTHER PUBLICATIONS

International Search Report, dated Apr. 21, 2016 in corresponding International Application No. PCT/RU15/000831.
International Preliminary Report on Patentability, dated Mar. 30, 2017 in corresponding International Application No. PCT/RU15/000831.
Extended European Search Report dated Sep. 8, 2017 in European Application No. 15866203.1.
Liu et al., "Cytokine interactions in mesenchymal stem cells from cord blood", Cytokine, 32:270-279 (2005).
International Search Report dated Oct. 19, 2017 in International (PCT) Application No. PCT/RU2017/000381.
Written Opinion of the International Searching Authority dated Oct. 19, 2017 in International (PCT) Application No. PCT/RU2017/000381.
Gnecchi et al., "Evidence supporting paracrine hypothesis for Aktmodified mesenchymal stem cell-mediated cardiac protection and functional improvement", The FASEB Journal, 20:661-669 (2006).
Pawitan, "Prospect of Stem Cell Conditioned Medium in Regenerative Medicine", BioMed Research International, vol. 2014:1-14 (2014).
Karaoz et al., "Characterization of mesenchymal stem cells from rat bone marrow: ultrastructural properties, differentiation potential and immunophenotypic markers", Histochem Cell Biol, 132(5):533-546 (2009).
Oshita et al., "Human Mesenchymal Stem Cells Inhibit Osteoclastogenesis Through Osteoprotegerin Production", Arthritis & Rheumatism, 63(6):1658-1667 (2011).
Gnecchi et al., "Paracrine action accounts for marked protection of ischemic heart by Akt-modified mesenchymal stem cells", Nature Medicine, 11(4):367-368 (2005).
Boomsma et al., "Mesenchymal Stem Cells Secrete Multiple Cytokines That Promote Angiogenesis and Have Contrasting Effects on Chemotaxis and Apoptosis", PLoS ONE, 7(4):1-8 e35685 (2012).
Chen et al., "Paracrine Factors of Mesenchymal Stem Cells Recruit Macrophages and Endothelial Lineage Cells and Enhance Wound Healing", PLoS ONE, 3(4):1-12 e1886 (2008).
Henson et al., "Karyotypic analysis of adult pluripotent stem cells", Histol Histopathol, 20:769-784 (2005).
Li et al., "Expression and secretion of interleukin-$\beta$, tumour necrosis factor-$\alpha$ and interleukin-10 by hypoxia- and serum-deprivation-stimulated mesenchymal stem cells: Implications for their paracrine roles", FEBS Journal, 277:3688-3698 (2010).
Chen et al., "Conditioned Medium from Hypoxic Bone Marrow-Derived Mesenchymal Stem Cells Enhances Wound Healing in Mice", PLoS ONE, 9(4):1-12 e96161 (2014).
Mishra et al., "Cell-free derivatives from mesenchymal stem cells are effective in wound therapy", World Journal of Stem Cells, 4(5):35-43 (2012).
Singer et al., "Cutaneous Wound Healing", The New England Journal of Medicine, 341(10):738-746 (1999).
Cantinieaux et al., "Conditioned Medium from Bone Marrow-Derived Mesenchymal Stem Cells Improves Recovery after Spinal Cord Injury in Rats: An Original Strategy to Avoid Cell Transplantation", PLoS ONE, 8(8):1-15 e69515 (2013).
Communication pursuant to Article 94(3) EPC dated Nov. 8, 2019 in European Patent Application No. 15 866 203.1.
Meirelles et al., "Mechanisms involved in the therapeutic properties of mesenchymal stem cells", Cytokine & Growth Factor Reviews, 2009, vol. 20, pp. 419-427.
Hwang et al., "Comparison of Cytokine Expression in Mesenchymal Stem Cells from Human Placenta, Cord Blood, and Bone Marrow", J. Korean Med. Sci., 2009, vol. 24, pp. 547-554.
Notification of Reasons for Refusal dated Oct. 29, 2019 in Japanese Patent Application No. 2017-547369, with English-language translation.
Xing et al., "Inflammatory Microenvironment Changes the Secretory Profile of Mesenchymal Stem Cells to Recruit Mesenchymal Stem Cells", Cellular Physiology and Biochemistry, 2014, vol. 33, pp. 905-919.
Noort et al., "Angiogenic factors produced by fetal lung mesenchymal stromal cells", in Progenitor Cells and Hypoxia in Angiogenesis, 2011, Chapter 6, pp. 173-193.
Li et al., "Mechanical load modulates chondrogenesis of human mesenchymal stem cells through the TGF-B pathway", J. Cell. Mol. Med., 2010, vol. 14, No. 6A, pp. 1338-1346.

\* cited by examiner

STEM CELL MATERIAL AND METHOD OF MANUFACTURING

FIELD OF THE INVENTION

Compositions and methods consistent with embodiments of the present invention generally concern at least the fields of cell biology, molecular biology, and medicine. More particularly, embodiments of the present invention relate to stem cells, stem cell conditioned culture media, methods of obtaining stem cell conditioned culture media, as well as applications for stem cells and stem cell conditioned culture media.

BACKGROUND

Mesenchymal stem cells, or MSCs, are multipotent stromal cells that have potential to differentiate into mesenchymal cell types, e.g. adipocytes, chondrocytes and osteocytes. MSCs have a great capacity for self-renewal while maintaining their multipotency. Bone marrow MSCs are currently being applied in clinical trials for a variety of treatments. Procedures for isolating, purifying, and replicating MSCs in culture are well known in the art.

MSCs can be cultured using beads, in monolayer (i.e. two-dimensions) or three-dimensional systems. These standard methods enable the growth of MSCs in conditions closely resembling their physiological environments. It has been documented that MSC behavior can vary between in vivo and in vitro settings. The differences between varying MSC lines have typically been attributed to differences in isolation techniques and in vitro culture conditions. For example, variation in growth conditions can impact cell behavior in vitro, including impacting the expression of cell surface markers. The expression of specific markers on the surfaces of cells can be used to differentiate between varying cell lines or to confirm the lineage of the cell line.

All cells (including MSCs) produce biological products during culture. For example, MCS's are known to produce over 200 unique proteins during culture. The specific biological products produced by MSCs during culture can be used to characterize and distinguish between various MSCs. However, even when MSCs from the same source are used, differences in isolation techniques and in vitro culture conditions can impact and change the production of secreted biological products. Of course, it is also known that deviations from the ideal cell growth conditions can lead to senescence and loss of culture.

SUMMARY OF THE INVENTION

According to one aspect of the present invention, there is provided a unique line of mesenchymal stem cells derived from the bone marrow of a Wistar rat that has one or more of certain characteristics. For example, when $0.7 \times 10^6$ cells are seeded into a 75 cm² flask and cultured for at least 96 hours, the line of mesenchymal stem cells can: (a) produce at least 4.5 mM of lactate within 24 hours of media exchange; (b) produce at least 150 pg/ml of GRO/KC within 24 hours of media exchange; (c) produce less than 250 pg/ml of OPG following 24 hours after media exchange; or (d) produce less than 80 pg/ml of TGF-β3 following 24 hours after media exchange. In accordance with another aspect, when $0.7 \times 10^6$ of the cells are seeded into a 75 cm² flask and cultured for at least 150 hours: (e) the pH of the culture medium decreases to below 7.0 within 24 hours of media exchange; or (f) the pH of the culture medium decreases by at least 0.4 units from the pH of the culture medium in the absence of cells within 24 hours of the culture medium exchange. The culture medium may be RPMI-1640 culture medium supplemented with 5% $CO_2$. In addition, the same stem cell line can undergo at least one population doubling at a pH of below 7.05. The stem cell line may also be characterized by the positive expression of CD29 and CD44 markers and negative expression of CD11b and CD45 markers.

A separate aspect of the invention relates to a conditioned medium, which can be prepared by maintaining a plurality of the unique stem cells in a culture medium for a specific conditioning period. In one aspect, the culture medium is RPMI-1640 supplemented with 5% $CO_2$. The cells may be maintained in the culture medium under various conditions, including an atmospheric concentration of $CO_2$ or in hypoxic conditions. According to aspects of the invention, the conditioning period may vary. For example, the conditioning period can be at least 12 hours, or it can be a period of time sufficient for the conditioned medium to contain at least 150 pg/mL of GRO/KC. In another aspect of the invention, the conditioned medium can contain at least one of the following: (a) at least 500 pg/mL of GRO/KC; (b) at least of 4000 pg/ml VEGF; (c) less than 250 pg/ml of OPG; or (d) less than 80 pg/ml of TGF-03.

Another aspect of the invention relates to a composition that includes the unique stem cell line or a culture medium conditioned by the unique cells. The composition may also include an appropriate carrier. The carrier may include a liquid, cream, aerosol, lotion, ointment, hydrogel, but is not limited thereto. In some aspects of the invention, the composition may be processed to remove some or all of the stem cells. In another aspect, the composition may include a conditioned medium that has less than 250 pg/mL of OPG or less than 80 pg/ml of TGF-β3.

According to aspects of the invention, the unique stem cell line, the conditioned medium, or the composition may be administered to a subject by injection, implantation, or by topical application. According to other aspects of the invention, the cells, the conditioned medium or the composition may be applied to a suture, bandage, knitted mesh, implant, stent, graft, a wet wipe, or periodontal pad, or other applicator devices. The cells, the conditioned medium, or the composition has a variety of uses, including, for example, burn treatment, skin care, angiogenesis, vasculogenesis, healing of organs or tissue, cosmetics, tissue inflammation, bacterial infections, wound applications, diabetes, pharmaceutical and ophthalmological applications, scar reductions, stimulating hair growth, in immunotherapy applications and for immunocorrection therapy, skin, bone marrow, or organ transplants, the treatment of organs or tissue, or for the treatment of other illnesses of humans or animals.

BRIEF DESCRIPTION OF THE DRAWINGS

The above and/or other aspects of the present invention will become more apparent by describing in detail examples of embodiments thereof with reference to the attached drawings in which.

DETAILED DESCRIPTION

Hereinafter, various examples of embodiments of the present invention will be explained with reference to the attached drawings. Aspects of the invention may be embodied in various forms without being limited to the embodiments set forth herein. It should be understood that any headings or subheadings used throughout the specification are provided for convenience only and shall not in any way limit the scope or meaning of the claims. Finally, it should be understood that, as used in the specification and the appended claims, the singular forms "a," "an" and "the" include plural referents unless the context clearly dictates otherwise.

One embodiment of the present invention relates to a novel mesenchymal stem cell line (hereinafter the "hb-MSC" line). A sample of the hb-MSC line was deposited with the Russian National Collection of Industrial Microorganisms (VKPM), located as 1 Dorozhny proezd 1, Moscow 117545, Russia, on Oct. 21, 2014. The deposit was given accession number H-154. The cell line is deposited under the name MSCRO5P09. The expression of cell surface markers of the hb-MSC line is consistent with those of a mesenchymal stem cell.

Another embodiment of the present invention relates to a medium conditioned by hb-MSCs and the method of obtaining the same. The conditioned medium contains a myriad of biological products, small molecules and exosomes capable of multiple biological functions.

A further embodiment relates to an hb-MSC composition. The hb-MSC composition may include: (1) hb-MSCs, a medium conditioned by culture of hb-MSCs, or any combination thereof; and (2) an appropriate carrier. The hb-MSCs, the medium conditioned by hb-MSCs and the hb-MSCs composition may be used in any state, delivered using any method known in the art, and used in a variety of applications.

Cells are passaged in vitro using a culture medium. Suitable media include, but are not limited to RPMI-1640, Dulbecco's Modified Eagle's Medium (DMEM), Ham's F12, Iscove's, McCoy's, or any other media that contains sufficient nutrients for cell growth. Such media can be prepared or obtained from commercial sources.

Depriving mesenchymal cells of their preferred growth environment typically results in decreased or stopped cell proliferation, loss of plastic adherence, and/or change in cell morphology. One important variable related to cell growth is the pH of the environment during cell proliferation. Typically, stem cells do not grow (or experience reduced proliferation rates) when conditions in culture deviate from physiological pH. For that reason, the culture medium typically acts as a buffer during cell culture. All cells produce and require small amounts of $CO_2$ for growth and survival. In some examples of culture media, dissolved $CO_2$ is in equilibrium with bicarbonate ions using the $CO_2$/bicarbonate reaction to buffer the pH of the medium. $CO_2$ dissolves freely into the medium and reacts with water to form carbonic acid. As the cells metabolize and produce more $CO_2$, the pH of the medium decreases. The optimal pH range of 7.2 to 7.4 can be maintained by supplementing the medium with sodium bicarbonate ($NaHCO_3$) and regulating the level of $CO_2$ in the atmosphere above the medium. The buffering capacity of the medium is determined by the amount of $NaHCO_3$. In general, 5% supplemental $CO_2$ is prescribed to achieve the optimal pH at a buffering capacity set by 1.2 to 2.2 g/L of $NaHCO_3$. As another example, to achieve the optimal pH at the buffering capacity set by 3.7 g/L of $NaHCO_3$, 10% supplemental $CO_2$ is prescribed. If the amount of supplemental $CO_2$ is below the buffering capacity of the medium, the pH of the medium may not be maintained at the appropriate levels, which can lead to senescence.

The cell culture medium may also include additional components such as vitamins, growth factors, hormones, proteins, sugars, and/or anti-oxidants, as necessary to support or maintain the desired cell culture. It should be understood that sera, such as fetal bovine serum (FBS), may be added. For example, 10% supplemental FBS could be added to the media, or plasma can be added in the same amount as animal serum. Alternatively, the cells could also be maintained and propagated in culture in the absence of supplemental serum and/or supplemental plasma. Media conditioned by cells may also be used in place of, or in addition to the culture media.

The hb-MSC line may be isolated from the bone marrow of a Wistar rat. The method of isolating the hb-MSC line generally includes at least: (1) obtaining Passage 1 cells from primary rat bone marrow cells; (2) seeding p1 rat mesenchymal stem cells in an appropriate flask; (3) a first incubation step, wherein the cells are incubated at a first predetermined $CO_2$ concentration for a first incubating time period; (4) a second incubation step, wherein the cells are incubated at a second predetermined $CO_2$ concentration for a second incubating time period; (5) collection of hb-MSCs.

Primary rat bone marrow stem cells can be harvested from the bone marrow of Wistar rat tibia or femurs according to well-known methods. Following cell harvest, the cell pellet may be re-suspended, seeded onto plastic tissue culture flasks and incubated in culture media (e.g. RPMI-1640 supplemented with 10% FBS) at 37° C. in a 5% $CO_2$ humidified atmosphere. The adherent cells grown to approximately 70% confluence are termed Passage No. 1 (p1).

In one embodiment, the first predetermined concentration of $CO_2$ may be set to match the $CO_2$ concentration prescribed for the buffering capacity of the media, as typically determined by the media manufacturer. For example, the first predetermined $CO_2$ concentration may be set to 5% when RPMI-1640 media is used for culture. In the same embodiment, the second predetermined concentration of $CO_2$ may be reduced by at least 50% from the $CO_2$ concentration prescribed for the buffering capacity of the media, as typically determined by the media manufacturer. For RPMI-1640 media the prescribed concentration of $CO_2$ is 5%. Therefore, according to one embodiment of the method, the second predetermined concentration of $CO_2$ should be set to below 2.5%. In another embodiment, the second predetermined concentration may be set to an atmospheric concentration of $CO_2$ (i.e. approximately 0.03% $CO_2$). One of ordinary skill in the art will understand that if the second predetermined concentration of $CO_2$ in the culture is increased, the second incubating time period may need to be increased (for example, one or more additional passages may be required) in order to isolate the hb-MSC line.

In one embodiment, the first incubating time period may be between zero to four cell passages. It should be understood that where the first incubating time period is zero passages, the first incubation step is skipped entirely. In another embodiment, the first incubating time period is a period between the number of hours required to achieve one population doubling (e.g. about 20-48 hours) to about 700 hours in culture. In one embodiment, the second incubating time period may be between one to eight cell passages. In a further embodiment, the second incubating time period is a period between the number of hours required to achieve one population doubling (e.g. about 20-48 hours) to about 2500 hours in culture. For example, the cells may undergo four passages in 0.03% $CO_2$ atmosphere in RPMI-1640 with 10% FBS. One of ordinary skill in the art will understand that the concentration of $CO_2$ may be adjusted during either incubation step as necessary.

A "passage" should be understood as the redistribution of cells, with or without dilution, from one culture flask to another culture flask containing fresh culture media. For example, a single cell passage may include: (1) seeding cells onto the surface of culture flask (e.g. approximately $2.0 \times 10^6$ cells on a 175 $cm^2$ surface area); (2) adding culture media (e.g. RPMI-1640); (3) setting a specified atmosphere of $CO_2$; (4) placing the culture flask in an incubator set to the appropriate temperature (e.g. 37° C.); (5) maintaining cells in the culture flask for predetermined period ("predetermined period of culture"); (6) supplying fresh culture media as necessary for cell growth; and (7) detaching and re-seeding cells.

For each passage, the cells are maintained in a culture medium where the predetermined period of culture is between about 30-700 hours. In one embodiment, the predetermined period of culture is less than 96 hours. In another embodiment, the predetermined period of culture is between about 96 to 168 hours. In yet a further embodiment, the predetermined period of culture is greater than 168 hours. Additionally, the predetermined period of culture may be based on cell confluence. In one embodiment, the predetermined period of culture is the time necessary for the cells to reach approximately 50% confluence. In another embodiment, cells are passaged after reaching between approximately 50% and 70% confluence. In a further embodiment, cells are passaged after reaching approximately 70% confluence.

The hb-MSC line may be isolated by culturing the cells in any number of dimensions (D). For example, the cells may be cultured using beads (OD), monolayers (2D), or 3D scaffolds. The hb-MSC line may also be isolated using a variety of systems. The hb-MSC line may be isolated using an open container system or a closed container system or a combination thereof. In one embodiment, the hb-MSC line may be isolated using a closed container system. In the closed container system, the cell culture flask is closed with an impermeable cap that can prevent access to supplemental $CO_2$. In another embodiment, hb-MSC line may be isolated using an open flask inside of a cell culture chamber that allows for control of $CO_2$ concentration. In another embodiment, the hb-MSC line may be isolated in a flask closed with a gas-permeable membrane, within a cell culture chamber that allows for control of $CO_2$ concentration.

One of ordinary skill in the art will understand that the various methods of culturing cells described above are provided as examples only and may not be used to limit the scope of any claims. One of ordinary skill in the art also will understand that the procedures, incubation periods, culturing periods, media, sera or $CO_2$ concentrations and other variables may need to vary to account for the behavior of cells during culturing.

Another embodiment of the present invention relates to the unique hb-MSC line. Cell surface marker expression can be used to confirm the mesenchymal nature of this line. Cell surface markers may be identified using any suitable method, including, for example, flow cytometry. As described in Example 4 and shown in FIG. 1, the method of obtaining hb-MSCs does not result in a change to the surface markers of the hb-MSCs, which can lead to a conclusion that hb-MSCs exhibit surface markers consistent with those of a rat bone marrow mesenchymal stem cell.

Figure 2:
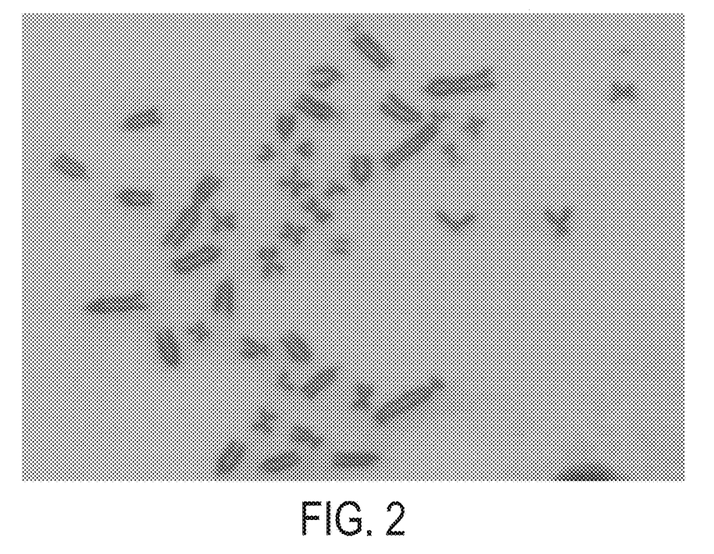
FIG. 2 illustrates Giemsa stained chromosomes from hb-MSCs at Passage No. 9 (p9).
Figure 3:
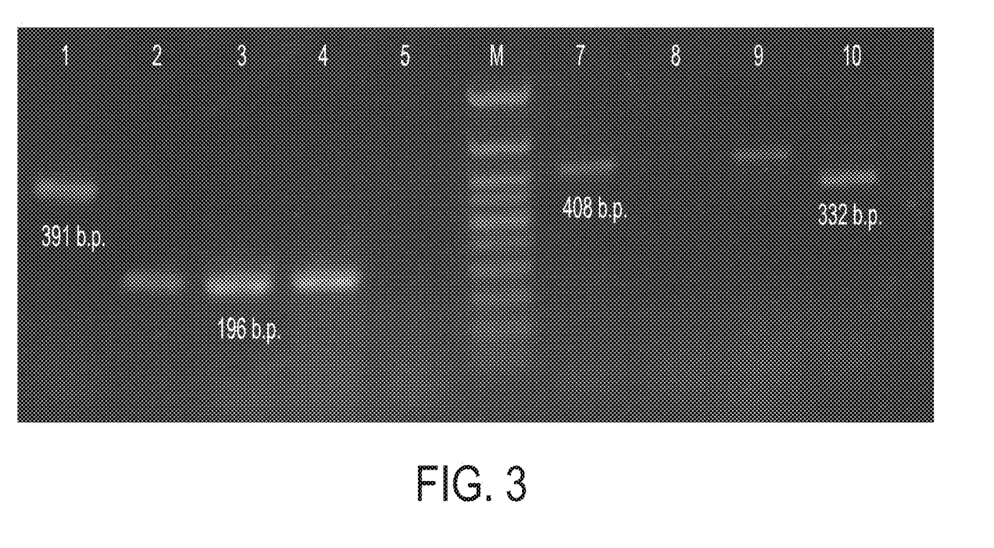
FIG. 3 illustrates the electrophoretograms of the PCR analysis of hb-MSCs and controls.

FIG. 2 illustrates the Giemsa stained chromosomes from hb-MSCs at Passage No. 9 (p9), while FIG. 3 illustrates the results of polymerase chain reaction (PCR) analysis. COX-1 and VN1R1 genes were used as markers for rat mitochondrial and nuclear DNA, respectively. At Passage No. 9, the karyotype is normal diploid (i.e. 2n=42). As described in Example 1 below, PCR analysis of the cell line confirmed that these are rat cells. One of ordinary skill in the art will understand that cells may be maintained for any number of passages, provided that karyotype analysis confirms the genetic stability of the cells.

The hb-MSC line differs significantly from other lines of stem cells obtained from rats, as can be illustrated using a number of different characterization methods. Rat mesenchymal stem cells obtained under standard conditions were cultured to show the differences between the typical rat mesenchymal stem cell and the unique hb-MSC line. The typical rat mesenchymal cell line prepared for purposes of this comparison was termed the rb-MSC line. To obtain the rb-MSC line, p1 rat mesenchymal cells were passaged according to standard conditions known in the art, as described in Example 2.

Example 7 (and FIG. 6) shows the difference between the pH of the medium of the hb-MSC and the rb-MSC line, which can be used to differentiate between the two lines. In another comparison, the hb-MSC line may be differentiated from the rb-MSC line by the total concentration of lactate in culture. Another way to differentiate the hb-MSC line from the rb-MSC line is by comparing various factors found in media conditioned by each respective line, as explained in Example 8 (and shown in Table 3). Of course, the hb-MSC line may also be characterized by other methods known to one of ordinary skill in the art.

Embodiments of the invention also relate to cells or cell lines differentiated from hb-MSCs. The cell lines can include adipocytes, chondrocytes, osteocytes, or other cells. Methods of differentiating to adipocytes, chondrocytes, osteocytes are well known in the art. Methods for genetically modifying stem cells are also well known. Stem cell lines made from genetically modified hb-MSCs and any cell lines differentiated from the genetically modified hb-MSCs are also within the scope of the invention.

One of ordinary skill in the art will understand that the various methods of characterizing hb-MSCs are provided for illustrative purposes only. Embodiments of hb-MSCs do not have to satisfy each of the various disclosed characterization methods, and some embodiments may satisfy only one or more of the characterization methods disclosed herein.

One embodiment of the invention relates to a culture medium conditioned by hb-MSCs, hereinafter termed "hb-MSC conditioned medium." In one embodiment, the conditioned medium may be produced by: (1) seeding a plurality of hb-MSCs into an appropriate flask; (2) providing a culture medium; (3) maintaining the hb-MSCs in culture media for a conditioning period; and (4) collecting the conditioned medium. The conditioning period may be hours, days, or even weeks, during which time the culture medium becomes enriched with biological products. When appropriate (e.g. once the medium is conditioned so that biological products such as growth factors, proteins and vesicles have reached desirable levels in the medium), the conditioned medium can be collected. For example, the conditioned medium may be collected after the hb-MSCs have been cultured for 3, 6, 24, 30, 48, 48, 54, 72, 96, 120, 144, 168, 192, 216, 240, 264, 288, 312, or 366 hours, or some other time period. The conditioned media obtained by culturing hb-MSCs may be processed under sterile conditions or sterilized as needed. One of ordinary skill in the art will understand that collection of the conditioned medium prior to the attachment of cells to the flask used for culture will result in the removal of cells with the growth medium, which may not be desired depending on the application.

In one embodiment, the hb-MSCs may be re-used to condition additional media by adding culture media to the hb-MSCs after removal of the conditioned medium. One of ordinary skill in the art will understand that the number of times that the cells may be reused depends on the number of hours used to condition the medium as well as the confluence of the cells. It should be understood that the hb-MSC conditioned medium collected over different time periods (e.g. every 3, 6, 24, 30, 48, 48, 54, 72, 96, 120, 144, 168, 192, 216, 240, 264, 288, 312, or 366 hours, or some other time period), conditioned medium collected by re-using hb-MSCs within a single passage, or medium collected from different passages of hb-MSCs may be combined for purposes of forming a single hb-MSC conditioned medium.

Media conditioned by any cell may include various biological products secreted, excreted, released, or otherwise produced during culture. For example, the conditioned medium may include biological products, such as, growth factors, anti-inflammatory factors, signaling factors, hormones, regulatory factors, enzymes, vesicles including exosomes, or any other compounds. The method of cell culture and the pH of the media may impact the type and amount of biological products released by the cells. It should also be understood that the concentration of cells initially seeded may impact the amount of biological products present in the conditioned media. It will also be understood that the addition of supplemental sera will impact the starting concentration of factors in the media prior to being conditioned, as the sera contains certain amounts of various biological products. Measuring the concentration of these factors in medium conditioned by hb-MSCs shows that this medium is significantly different from medium conditioned by rb-MSCs. Commercially available assays can be used to measure the concentrations of factors produced by the cells (e.g. assays available from EMD Millipore or Eve Technologies). It should be understood that the exact measurement will depend on the antibody pairs used in the assays, and thus the detected concentration of factors may vary depending on the assay or measurement technique used. Example 8 describes a comparison of factor concentrations of the rb-MSC and hb-MSC lines at specified time periods.

In one embodiment, the conditioned medium may be formed by maintaining hb-MSCs in a $CO_2$ concentration prescribed for the buffering capacity of the media, as typically determined by the media manufacturer. For RPMI-1640 media, the prescribed concentration of $CO_2$ is 5%. In another embodiment, the conditioned medium may be formed by maintaining hb-MSCs in a concentration of $CO_2$ that is reduced by at least 50% from the $CO_2$ concentration prescribed for the buffering capacity of the media, as typically determined by the media manufacturer. In another embodiment, the conditioned medium may be formed by maintaining hb-MSCs at an atmospheric concentration of $CO_2$ (i.e. 0.03% $CO_2$).

In one embodiment, the conditioned medium may be formed by maintaining hb-MSCs in an atmospheric concentration of O2 (i.e. 17%). In another embodiment, the conditioned medium may be formed by maintaining hb-MSCs in a concentration of O2 reduced below 10%. In another embodiment, the conditioned medium may be formed by maintaining hb-MSCs in a concentration of O2 reduced below 2%. The use of a lowered concentration of O2 (hypoxic conditions) may be used, for example, to mimic the bone marrow environment in vivo.

In some embodiments, the conditioned medium may be used in concentrated form. For example, the conditioned medium may be concentrated by a factor between 1 and 100 using any known method in the art. The appropriate concentrations required will depend on the application of the conditioned medium.

In one embodiment, the neat collected conditioned medium is further processed to add/remove and/or concentrate/dilute specific biological products. The methods used for product isolation and purification should be selected such that optimal biological activity is maintained. For example, it may be desirous to purify a growth factor, regulatory factor, peptide hormone, antibody, exosome or any other desired biological compound. Such methods include, but are not limited to, gel chromatography, ion exchange, metal chelate affinity chromatography, high pressure liquid chromatography (HPLC), hydrophobic interaction chromatography, or centrifugation. In another embodiment, the exosomes or any other vesicles present in the conditioned medium may be concentrated in the conditioned medium or removed from the conditioned medium.

In another embodiment, the conditioned medium can be lyophilized. The lyophilized conditioned medium can be reconstituted utilizing any appropriate diluent including, without limitation, normal saline, phosphate buffered saline, cell culture media, conditioned cell culture media, water, or mixtures thereof. The conditioned medium may be reconstituted in the same concentration as the original conditioned medium. In a separate embodiment, the lyophilized conditioned medium can be reconstituted in a more concentrated form as compared to the original conditioned medium with the concentration factor varying from 1 to 100.

The hb-MSC line may be used to condition a wide variety of culture media. In some embodiments, the culture media may also be supplemented with additional fetal serum and/or plasma. In one embodiment, the medium is conditioned in the presence of 20% FBS. In another embodiment, the medium is conditioned in the presence of 10% FBS. In another embodiment, the medium is conditioned in the presence of 7% FBS. In another embodiment, the medium is conditioned in the presence of 3% FBS. In an alternate embodiment, the medium is conditioned in the absence of FBS. In other embodiments, after the cells have reached a specific confluence, a lowered concentration of serum or serum-free media may be used as a replacement, to form a low-serum or a serum-free conditioned medium.

Another embodiment of the present invention relates to an hb-MSC composition. The hb-MSC composition may include hb-MSCs, hb-MSC conditioned medium, or a combination thereof. The hb-MSC composition may also include an appropriate carrier. The total amount of hb-MSC conditioned medium in the hb-MSC composition can vary between 0.00001 to 99.99% by volume.

Embodiments of the hb-MSC composition may include hb-MSC conditioned medium combined with hb-MSCs, rb-MSCs, or other cells selected on the basis of the application/purpose of the medium. For example, the cells that may be added to the hb-MSC composition may include autologous cells, allogeneic cells or xenogeneic cells.

In a different embodiment, the hb-MSC composition may include hb-MSCs or hb-MSC conditioned medium combined with any other conditioned medium or any combination of conditioned media in any desired ratio. The hb-MSC composition may also include hb-MSCs or hb-MSC conditioned media in combination with media conditioned by autologous cells, allogeneic cells or xenogeneic cells. In another example, the hb-MSC conditioned media may be combined with media conditioned by human mesenchymal stem cells.

The hb-MSC composition should be kept free of contamination by bacteria, viruses, mycoplasma, or fungi. In one embodiment, this may be accomplished by sterile processing conditions during cell culture and processing. In another embodiment, the hb-MSC composition contains pharmaceutical preservatives to provide a level of antimicrobial activity. In some embodiments the preservatives may limit secondary bacterial, mycotic, or amoebal infections caused by contamination of solutions. In other embodiments the addition of preservatives prolongs the shelf life of the hb-MSCs or the hb-MSC conditioned media by preventing biodegradation and maintaining potency. In a non-limiting example, the preservatives can include detergents, oxidants, chelating agents, or metabolic inhibitors including pentavalent antimonials, quaternary ammoniums, and organomercurials. Examples of preservatives include thimerosol, cresols, formalin, benzalkonium chloride or benzyl alcohol.

In yet a further embodiment, the hb-MSC composition may be supplemented with anti-inflammatory agents, antibacterials, analgesics, antifungals, bactericides, disinfectants, vitamins, sunscreens, antibiotics, agents for combating free radicals, sequestering agents, basifying or acidifying agents, fragrances, surfactants, fillers, natural products or extracts of natural products. The supplements may include organic small molecules, organometallic compounds, polymers, inorganic salts, proteins, growth factors, chemokines, DNA, RNA, or enzymes. In further embodiments the medium may be supplemented with sugars, proteins, insulin, signaling proteins, or any additional small molecules, including coloring agents, flavoring agents, or sweeteners. The supplements can also contain minor amounts of additives, such as substances that enhance isotonicity or chemical stability.

One of ordinary skill in the art will understand that an appropriate carrier for the hb-MSC composition can include, for example, a liquid, cream, aerosol, lotion, ointment or hydrogel. These carriers may be based on the addition of aqueous excipients (including culture media), non-aqueous excipients, oils, standard fatty substances, conventional gelling agents, buffers, thickeners, suspension agents, emulsifiers, moisturizing agents, emollients, hydrophilic or lipophilic active agents. The amounts of these various ingredients will vary depending on the use of the hb-MSC composition and the effect desired. Of course, one of ordinary skill in the art will understand that the "appropriate carrier" may include a mixture of two or more carriers and/or other ingredients.

The hb-MSCs composition disclosed herein may be used for a variety of purposes, including, but not limited to, any research, diagnostic, therapeutic or commercial purpose. The hb-MSC composition may be used to treat a wide variety of conditions, including, for example, burn treatment, skin care, angiogenesis, vasculogenesis, healing of organs or tissue, cosmetics, tissue inflammation, bacterial infections, wound applications, diabetes, pharmaceutical and ophthalmological applications, scar reductions, stimulating hair growth, in immunotherapy applications and for immunocorrection therapy, skin, bone marrow, or organ transplants, the treatment of organs or tissue, or for the treatment of other illnesses of humans or animals.

As used herein, "treat" encompasses the cure of, remediation of, improvement of, lessening of the severity of, or reduction in the time course of, a disease, disorder or condition, or any parameter or symptom thereof. It should be understood that hb-MSCs, or hb-MSC conditioned medium, could be used for the same or similar purpose as the hb-MSC composition.

The hb-MSC composition may also be used for dermatological or cosmetic applications, in food supplements or animal feed supplements, for culturing cells, and in pharmaceutical applications. The hb-MSC composition may be used for preventative treatments, in response to an acute injury, or for the treatment of chronic injuries. In one embodiment, the hb-MSC composition may be used for the treatment of human illnesses or conditions. In another embodiment, the treatment may include veterinary applications.

In one embodiment, the hb-MSC composition may be advantageously used in the treatment of wounds, including skin wounds, broken bones, gastric or diabetic ulcers, pancreas, liver, kidney, spleen, blood vessel injuries and other internal or external wounds as well as healing burns. For example, the hb-MSC composition may be used in topical applications to promote and/or accelerate wound healing, as described in Example 5 and shown in FIGS. 4 and 5. In another embodiment, the hb-MSC composition could be used to treat wounds that would otherwise require surgical excision or drainage. For example, the hb-MSC composition may provide for increased perfusion of wound tissue.

The hb-MSC composition may be used in the cosmetic treatment of skin, including the treatment of wrinkles, frown lines, scarring, or to repair other skin conditions, such as those resulting from deleterious effects induced by UV light, and normal aging.

Delivery of the hb-MSC composition may be carried out in any known manner in the art. For example, some embodiments for such delivery may be site-specific, topical, oral, nasal, intravenous, subcutaneous, intradermal, transdermal, intramuscular or intraperitoneal administration. In an additional embodiment, the hb-MSC composition may be formulated for use in controlled, slow release vehicles.

It will be appreciated that the actual preferred amounts, modes of administration, and administration intervals of the hb-MSC composition in a specified case will vary according to the specific composition being utilized, the particular compositions formulated, the mode of application, the particular injury and subject being treated. Dosages for each specific case can be determined using conventional considerations, e.g. by means of an appropriate conventional pharmacological protocol. Physicians and formulators, skilled in the art of determining doses of pharmaceutical compounds, will be able to determine the appropriate dose.

The hb-MSC composition may be used in any state. For example, the hb-MSC composition may take the form of tablets, capsules, skin patches, inhalers, eye drops, nose drops, ear drops, liquid washes, suppositories, lotions, creams, ointments, injectables, gels, hydrogels, thin-films, powders, serums, salves, foundations, facial masks, lip care products, sunscreens, hair care products, such as shampoos, conditioners, including deep conditioners, hair care treatments, skin cleansers, exfoliants, compact formulations, or any other appropriate forms known to one of skill in the art.

In some embodiments, the hb-MSC composition may be used to coat sutures, medical equipment, or implantation devices. In another embodiment the hb-MSC composition may be combined with sutures, bandages, implants, stents, grafts, or in periodontal applications. The hb-MSC composition may also be used in wet wipes. The hb-MSC composition may also be added as wound filler or added to existing wound filling compositions to accelerate wound healing. In another embodiment, the hb-MSC composition may also be added to eye shadow, pancake makeup, compacts or other cosmetics.

In additional embodiments, liquid preparations of the hb-MSC composition may take the form of, for example, solutions, syrups or suspensions, or presented as a dry product for constitution with an appropriate carrier before use.

In another embodiment, the hb-MSC composition can be frozen for a set period of time. Alternatively, the hb-MSC composition can be lyophilized and frozen for a set period of time. Alternatively, the hb-MSC composition can be reconstituted as described above and frozen for a set period of time. Alternatively, the hb-MSC composition can be stored or kept at a temperature between room temperature (e.g. about 28° C.) and 0° C. The temperature range used is not intended to be exclusive, and one of skill in the art can envision alternative temperature ranges utilized depending on the nature of the application.

In another embodiment, the hb-MSC composition can be brought to room temperature before use. Alternatively, the hb-MSC composition can be applied at a temperature below room temperature. Alternatively, the hb-MSC composition can be utilized at a temperature above room temperature, as long as the temperature is not high enough to denature the biological material.

EXAMPLES

The following examples are included to demonstrate certain embodiments of the invention. It should be appreciated by those of skill in the art that the techniques disclosed in the examples below represent techniques discovered by the inventors, and may be considered to constitute modes for practicing certain embodiments of the invention. However, those of skill in the art should, in light of the present disclosure, appreciate that many changes can be made to the examples below without departing from the spirit and scope of the invention.

Example 1—Species Identification for Hb-MSC Cells

PCR analysis was used to confirm that the cells are indeed from a rat. For PCR analysis COX-1 and VN1R1 genes were used for mitochondrial and nuclear DNA, respectively. Amplification of the COX-1 gene was carried out using multiplex-PCR, while amplification of the VN1R1 gene was carried out using standard PCR. Blood sample from a 38 yr old human male, a 32 yr old human female and a Wistar rat were used as control. The DNA was isolated from the cell culture utilizing a commercially available kit (PREP-GS-GENETICS, DNA Technology, Russia), according to the manufacturer instructions. All primers are commercially available, and were purchased from Evrogen, LLC.

The specific primers used for the PCR analysis were:

```
COX1-human:
                                         (SEQ ID NO: 1)
f'-TAGACATCGTACTACACGACACG
and (SEQ ID NO: 2)
r'-TCCAGGTTTATGGAGGGTTC.

COX1-rat:
                                         (SEQ ID NO: 3)
f'-CGGCCACCCAGAAGTGTACATC
and (SEQ ID NO: 4)
r'-GGCTCGGGTGTCTACATCTAGG.

VN1R1-human:
                                         (SEQ ID NO: 5)
f'-TGGTCTGGGCCAGTGGCTCC
and (SEQ ID NO: 6)
r'-GAGTGTTTTCCTTGTCCTGCAGGCA.

VN1R1-rat:
                                         (SEQ ID NO: 7)
f'-AGAAGAGTTACTGGCCCAAGGGACA
and (SEQ ID NO: 8)
r'-GGGGCTGAACGCTGGGAAGC.
```

Electrophoresis of the PCR products was carried out on 2% agarose gel utilizing a SubCellGT electrophoresis system (Bio-Rad). The gel was visualized using an ECX-F15.0 (Vilber Lourmat) transilluminator. The electrophoretograms are shown in FIG. 3. Specifically, in FIG. 3, Lanes 1-5 show the COX1 gene base pairs. Lane 1 shows the result for control human DNA, while Lane 2 shows the result for control rat DNA. Lanes 3 and 4 show the results for hb-MSC samples. Lane 5 shows a negative control. Lanes 7-10 show the VN1R1 gene base pairs. Lane 10 shows a mixture of control human and control rat DNA. Lanes 9 and 7 show the results for hb-MSC samples. Lane 8 is the negative control. "M" signifies the DNA fragment marker lane. The electrophoresis confirms that the hb-MSCs were isolated from a rat and are not contaminated with material from human cells.

Example 2—Culture of rb-MSCs

Rat mesenchymal stem cells obtained under standard conditions were cultured and evaluated to show the differences between the unique isolated hb-MSC line and the typical rat mesenchymal stem cell (rb-MSCs).

Both the rb-MSC line and the hb-MSC line were isolated from primary cells collected from the bone marrow of Wistar rat tibias or femurs. Culturing of all cells took place under GMP conditions. In one embodiment, the procedure for obtaining the primary cells is as follows. The animals were anesthetized and euthanized. Under sterile conditions, both femurs and tibias from each rat were excised. Bone marrow was extruded by flushing with MEM-Earle medium supplemented with 15% fetal bovine serum (FBS). Marrow plug suspension was dispersed by pipetting, successively filtered through 70-μm mesh nylon filter, and centrifuged at 200 G for 10 min. The supernatant was discarded, and the cell pellet was re-suspended in the medium. The cells from one rat were seeded onto plastic flasks and incubated at 37°

C. in a 5% $CO_2$ humidified atmosphere. On the third day, red blood cells and other non-adherent cells were removed and fresh supplemented medium was added to allow further growth. The adherent cells grown to 70% confluence were defined as the primary culture cells (p1).

To obtain the rb-MSC line, p1 rat mesenchymal cells were passaged according to standard conditions known in the art and in accordance with the manufacturer guidelines specified for RPMI-1640. The p1 cells were washed with $Ca^{2+}$—$Mg^{2+}$-free Hanks solution (Sigma, USA, H9394-500 ml) and detached by incubating with 0.25% trypsin-EDTA solution (Sigma, USA, T4424-100 ml) for 5-10 min at 37° C. Next, 5% FBS (Sigma, USA, F6765) supplemented Hanks solution was added to inactivate the trypsin. The cells were centrifuged at 200 G for 10 min, re-suspended in 1-2 ml RPMI-1640 media supplemented with 15% FBS, and counted manually using a hemocytometer grid with Neubauer ruling. The cells were then plated as p2 in 75 $cm^2$ flasks at densities of $1.0 \times 10^6$ cells/flask, using RPMI-1640 medium (Sigma, USA, R5886) supplemented with 15% FBS (Sigma, USA, F6765), 100 units/ml penicillin-100 μg/ml streptomycin (Sigma, USA, P4458), 100 ng/ml amphotericin (Sigma, USA, A2942), 2 mM L-Glutamine (Sigma, USA, G7513), 0.005 ml/ml vitamins (100×) for RPMI-1640 medium (Sigma, USA, R7256), and 0.005 ml/ml amino acids for RPMI-1640 medium (Sigma, USA, R7131). The flask, having a permeable sterile filter cap, was incubated at 37° C. in humidified incubator with a 5% $CO_2$ atmosphere. The RPMI-1640 medium (supplemented with 15% FBS) was replaced every 3 days over a 10- to 14-day period (or upon reaching 70% confluence). Following Passage No. 2 (p2) the cells were plated in 175 $cm^2$ flasks at densities of $2 \times 10^6$ cells/flask, and RPMI-1640 supplemented with 10% FBS was used. For each subsequent passage, the cells were plated similarly and grown to 70% confluence. Following 70% confluence the cells were split and re-seeded within a plastic culture flask. Passage 5 (p5) rb-MSCs were used as the comparison to the hb-MSC line.

Example 3—Culture of Hb-MSC

To obtain the hb-MSC line, p1 rat mesenchymal cells were cultured according to the following method. First, the p1 cells were washed with $Ca^{2+}$—$Mg^{2+}$-free Hanks solution (Sigma, USA, H9394-500 ml) and detached by incubating with 0.25% trypsin-EDTA solution (Sigma, USA, T4424-100 ml) for 5-10 min at 37° C. Next, 5% FBS (Sigma, USA, F6765) supplemented Hanks solution was added to inactivate the trypsin. The cells were centrifuged at 200 G for 10 min, re-suspended in 1-2 ml RPMI-1640 media supplemented with 15% FBS, and counted manually using a hemocytometer grid with Neubauer ruling. The cells were then plated as p2 in 75 $cm^2$ flasks at densities of $1.0 \times 10^6$ cells/flask, using RPMI-1640 medium (Sigma, USA, R5886) supplemented with 15% FBS (Sigma, USA, F6765), 100 units/ml penicillin-100 μg/ml streptomycin (Sigma, USA, P4458), 100 ng/ml amphotericin (Sigma, USA, A2942), 2 mM L-Glutamine (Sigma, USA, G7513), 0.005 ml/ml vitamins (100×) for RPMI-1640 medium (Sigma, USA, R7256), and 0.005 ml/ml amino acids for RPMI-1640 medium (Sigma, USA, R7131). The flask, having a permeable sterile filter cap, was incubated at 37° C. in humidified incubator with a 5% $CO_2$ atmosphere. The RPMI-1640 medium supplemented with 15% FBS was replaced every 3 days over a 10- to 14-day period (or upon reaching 70% confluence).

Following Passage No. 2 (p2) the cells were plated in 175 $cm^2$ flasks at densities of $2 \times 10^6$ cells/flask, and RPMI-1640 supplemented with 10% FBS was used. The cultures continued to be grown at 37° C. in humidified incubator with a 5% $CO_2$ atmosphere. Following the third Passage (p3), the cells were passaged at a reduced $CO_2$ concentration. To reduce the $CO_2$ concentration, the culture flask was sealed with an impermeable cap under atmospheric $CO_2$ conditions and incubated at 37° C. No supplemental $CO_2$ was used in all of the following passages. As previously described, fresh RPMI-1640 medium supplemented with 10% FBS was added and replaced every 3 or 4 days for about 14 days. For each passage, the cells were plated similarly and grown to 70% confluence. Following 70% confluence the cells were split and re-seeded within a plastic culture flask. Passage 9 (p9) hb-MSCs were compared with rb-MSCs. PCR analysis (Nanodiagostika, LLC, RUS) confirmed that the hb-MSCs are free of contamination by bacteria, viruses, mycoplasma, or fungi.

The hb-MSC line was preserved utilizing 10% DMSO and 50% FBS medium at liquid nitrogen temperatures with a concentration between $3.0 \times 10^6$ to $5.0 \times 10^6$ cells in a 2 milliliter (ml) ampoule.

Example 4—Flow Cytometry Characterization of Hb-MSCs

Figure 1:
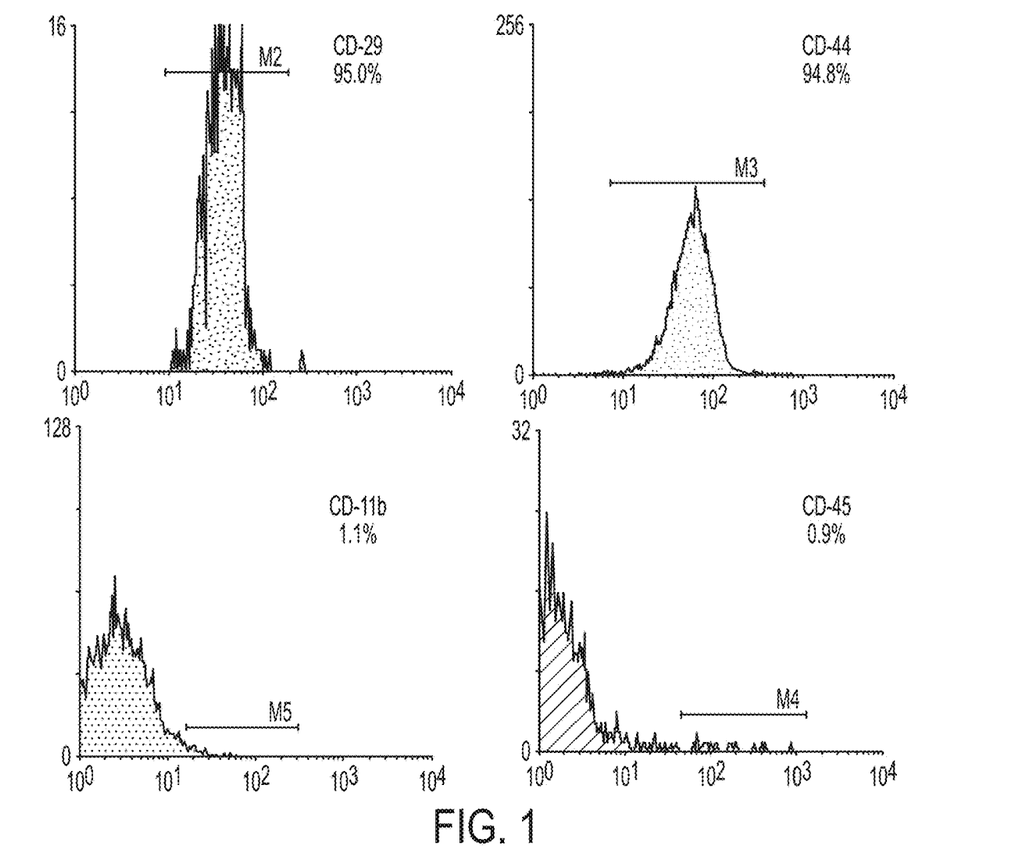
FIG. 1 illustrates the flow cytometry analysis of surface cell markers of hb-MSCs, including the marker type and the relative percent of markers.

A flow cytometry experiment was carried out to identify the cell surface markers of the hb-MSC and rb-MSC lines. For purpose of this experiment, 50 μl of the corresponding antibody was added to a 100 μl cell suspension. The suspension was vortexed for a period of five seconds (BioVortexV1, BioSan) and maintained at +4° C. for a period of 30 minutes in absence of light. Following incubation, the mixture was diluted with 500 μl of saline solution and washed twice via centrifugation to remove excess reagents. Each centrifugation was carried out at 400 G for a period of 10 minutes (ELMI). In each sample at least 10,000 counts were analyzed. The results were analyzed using WinMDI 2.7 analysis program and are shown in FIG. 1. A summary of the surface markers expressed by the rb-MSC and the hb-MSC lines is provided in Table 1 below.

TABLE 1

| rb-MSC and hb-MSC line surface markers | | |
|---|---|---|
| Cell Surface Marker | hb-MSC line | rb-MSC line |
| CD29 | 95.0% | 94.6% |
| CD44 | 94.8% | 98.7% |
| CD11b | <3% | <3% |
| CD45 | <3% | <3% |

Typical bone marrow rat mesenchymal cells exhibit positive expression of CD44, CD29 markers and negative expression of CD45, and CD11b markers. As shown in Table 1 above, the hb-MSC line exhibits surface markers consistent with that of a bone marrow mesenchymal stem cell of a rat. This demonstrates that the method of obtaining hb-MSCs does not result in a change to the surface markers of the cells.

Example 5—Morphometric Study of Wound Closure

Figure 4:
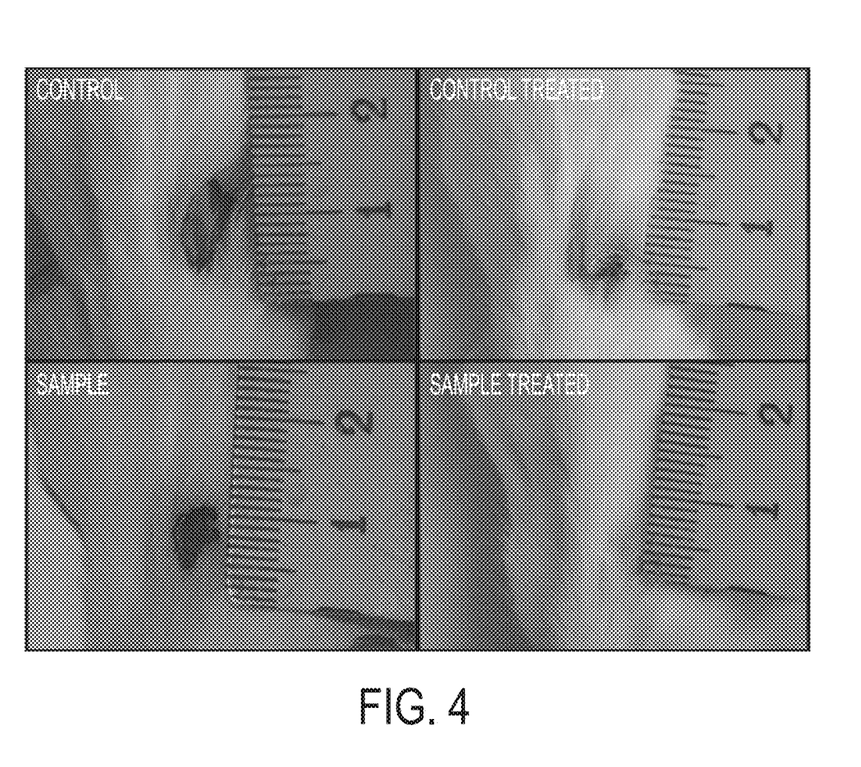
FIG. 4 shows a comparison of mouse wounds nine days after being treated by RPMI-1640 culture medium and by the hb-MSC composition.
Figure 5:
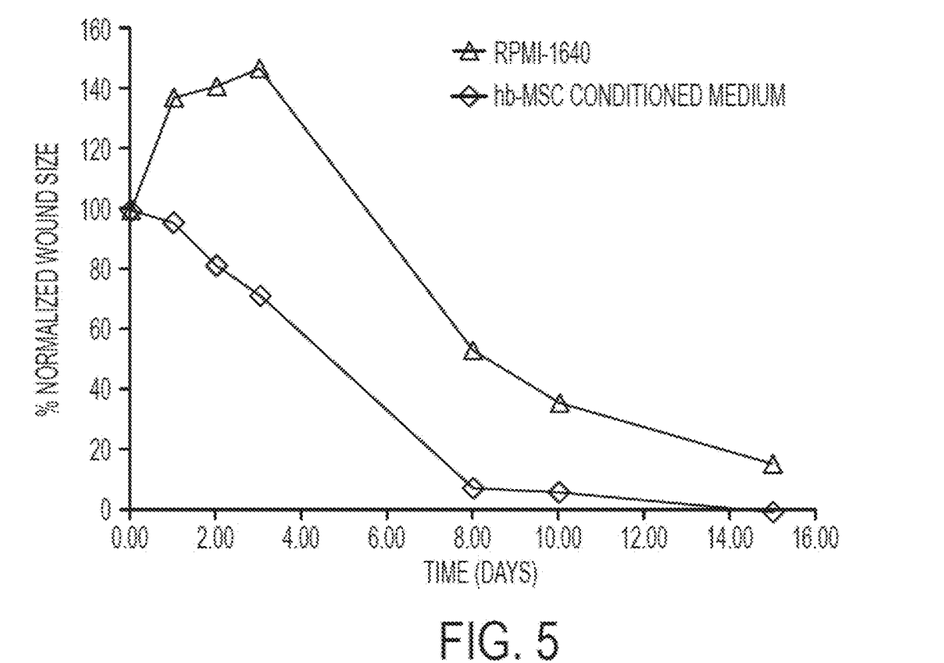
FIG. 5 shows the relative speed of wound closure for mouse wounds treated by RPMI-1640 culture medium and by the hb-MSC composition.

A morphometric study was undertaken to follow the wound healing process of laboratory mice. All animal experiments were carried out in the veterinary surgery department of Moscow State Academy of Veterinary Medicine and Biotechnology named after K.I. Scriabin. White laboratory mice 3 to 5 months in age weighing approximately 22-25 grams were used for all experiments. A total of six mice were used in each experiment. An incision of approximately 0.5 cm in diameter was made in a freshly shaved shoulder blade area of each anesthetized animal. Following the incision, the animals were sorted into control and sample groups, with three mice per group. Each wound was photographed to obtain digital morphometric parameters. Thirty minutes following the incision each wound was treated with a 50 µl drop of either RPMI-1640 or the hb-MSC composition. In this example, the hb-MSC composition included the hb-MSC conditioned medium as described in Example 8, wherein the conditioned medium collected at each of the different conditioning time periods (96, 144, 192, 216, 240, 264, and 288 hours) was combined in a single container. The composition also included benzalkonium chloride (BEK) as a preservative, and Triton X-100 as a surfactant. The wound size was measured once each day for a period of 15 days. The hb-MSC composition and RPMI-1640 were applied to each animal in the respective groups once per day following wound assessment. The digital images showing the comparative healing process of wounds treated with the hb-MSC composition and the RPMI-1640 medium are shown in FIG. 4. FIG. 4 shows a mouse from the control group (treated with RPMI-1640) on day 1 of treatment and the same mouse on day 9 of treatment. FIG. 4 also shows a mouse from the sample group (treated with the hb-MSC composition) on day 1 of treatment and the same mouse on day 9 of treatment. The effect of the treatment on average wound size using the hb-MSC composition vs. RPMI-1640 is illustrated in FIG. 5.

Example 6—Therapeutic Effect of the Hb-MSC Composition

In order to test the therapeutic effect of the hb-MSC composition, experiment were conducted on a variety of animals, including canines (65+), felines (80+), equines (40+), livestock (25+), rodents (200+), and ayes (15+). The hb-MSC composition was used to treat a wide variety of conditions in the above test subjects. The hb-MSC composition used in this example was the same as in Example 5. These treatments included: 1) wound applications, including post-operative incision sites; 2) burn treatments, including chemical burns; 3) ulcers including diabetic ulcers; 4) fistulas, 5) tissue inflammation or bacterial infections, including purulent inflammations, conjunctivitis, keratitis, mastitis, phlegmon, gastritis, and dermatitis; 6) orthopedic applications, including bone fractures; and 7) treatment of varying tissues including skin, ligaments, and muscle tissue. In the experiments, the hb-MSC composition was delivered by the following methods: topical, oral, nasal, intravenous, subcutaneous, intradermal, transdermal, intramuscular and intraperitoneal. Additionally, the hb-MSC composition was applied utilizing sterile napkins, as an aerosol, and by direct application to the affected area (including by using teat dip cups). The hb-MSC composition was effective in treating all of the above conditions, showing improved regenerative effects, wound closure speed, significant reduction of inflammation and local bacterial colonization, antimicrobial effects, angiogenesis and vasculogenesis, reduced scarring of tissue and a restoration of hair follicles in the affected area. The substantial regenerative effects observed in these experiments were consistent with the results of the mouse wound experiments described in Example 5. In all cases, the animals remained healthy after treatment with the hb-MSC composition. For all cases, toxicity, irritation, sensitization and bio-accumulation were assessed. All tracked indicators for all animals within 30 days of administration of the hb-MSC composition remained within the normal range as assessed by blood tests. Histology of the kidneys liver, lungs, spleen, intestines, and soft tissues did not demonstrate any signs of acute or chronic toxicity from the application of the hb-MSC composition. There also were no recorded instances of allergic reactions, infections, or other negative side effects. Taken together, these experiments demonstrate that the hb-MSC composition may be used to safely and effectively treat a wide variety of conditions in humans and animals, including burn treatment, skin care, angiogenesis, vasculogenesis, healing of organs or tissue, cosmetics, tissue inflammation, bacterial infections, wound applications, diabetes, pharmaceutical and ophthalmological applications, scar reductions, stimulating hair growth, in immunotherapy applications and for immunocorrection therapy, skin, bone marrow, or organ transplants, the treatment of organs or tissue, or for the treatment of other illnesses.

Example 7—Analysis of Culture Media Conditioned by the Rb-MSC and Hb-MSC Cell Lines To compare the impact of the hb-MSCs and rb-MSCs on the culture medium nine (9) separate 75 $cm^2$ flasks of each cell line were plated at a density of $0.7 \times 10^6$ cells/flask. The cells were passaged in RPMI-1640/10% FBS supplemented with 5% $CO_2$ in an incubator set to 37° C. The cell flasks were closed with a gas-permeable cap. A total of 9 time periods were analyzed: 24, 48, 96, 144, 192, 216, 240, 264, and 288 hours. A single flask of cells was analyzed at each prescribed time period. The media was exchanged in all remaining vials following three days (72 hours), five days (120 hours), seven days (168 hours), and daily thereafter. Lactate concentration and pH of the medium was measured at each of the nine periods. With the exception of the 48 hour measurement, the periods were selected so that measurement would take place 24 hours after the media was exchanged. Lactate was measured utilizing a biochemical analyzer, in triplicate, with a lactate characterization kit from SPINREACT. pH was measured using an electronic pH meter (METTLER TOLEDO InLab Versatile Pro). Cell count was also measured at each of the periods, and the cells underwent at least one population doubling at a pH below 7.05.

Figure 6:
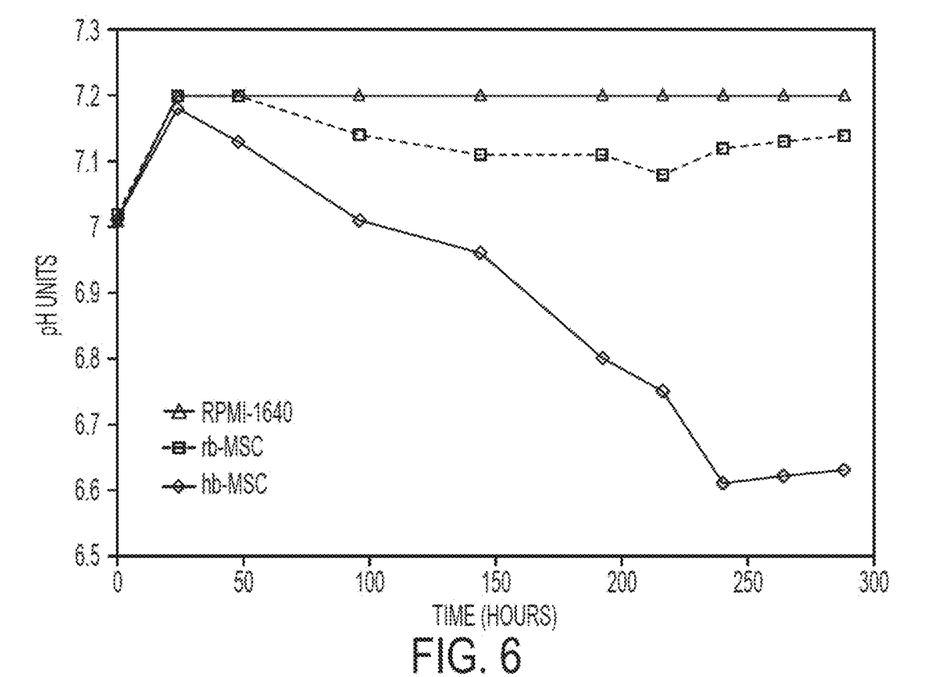
FIG. 6 illustrates the change in pH over time for RPMI-1640 media, rb-MSC conditioned media, and hb-MSC conditioned media.
Figure 7:
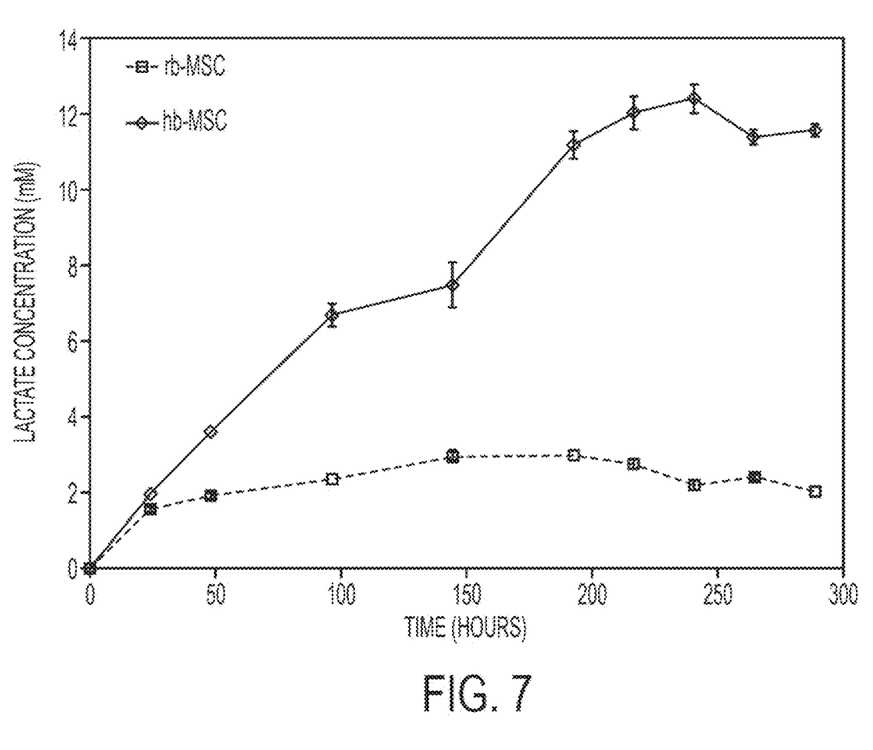
FIG. 7 illustrates the change in the lactate concentration (mM) during cell culture for hb-MSCs and rb-MSCs.

FIG. 6 illustrates the change in pH over time for pure RPMI-1640 culture media, rb-MSC conditioned media, and hb-MSC conditioned media measured at the times of cell collection described in this Example. FIG. 7 shows the change in the lactate concentration (mM) for rb-MSC and hb-MSC lines during culture. The error bars represent one standard deviation in lactate concentration. The following table, which is based on the data in FIGS. 6 and 7, shows a comparison of the various measurements for rb-MSCs and hb-MSCs in this Example.

TABLE 2

Methods of differentiation for hb-MSC and rb-MSC lines

| Method of Differentiation | rb-MSCs | hb-MSCs |
|---|---|---|
| pH of media following at least 150 hours in culture (within 24 hours of media exchange) | >7.05 (at all times) | <7.0 |
| Maximum deviation from pH of RPMI-1640 media (within 24 hours of media exchange) | <0.15 | >0.4 |
| Lactate concentration of media following at least 96 hours in culture (within 24 hours of media exchange) | <3 mM | >4 mM |
| Number of population doublings at a pH below 7.05 | 0 | >1 |

Example 8—Comparison of Factors in Media Conditioned by Rb-MSC and Hb-MSC Cell Lines The rb-MSC and hb-MSC lines may be distinguished by comparing the factors produced by each line when the line is maintained in culture media. To compare the factors produced by the hb-MSCs and rb-MSCs, seven (7) separate 75 cm$^2$ flasks of each cell line were plated at a density of $0.7 \times 10^6$ cells/flask. The cells were passaged in RPMI-1640/10% FBS supplemented with 5% $CO_2$ in an incubator set to 37° C. It will be understood by one of ordinary skill in the art that the addition of supplemental sera will impact the starting concentration of factors in the media prior to being conditioned. The cell flasks were closed with a gas-permeable cap. A total of 7 time periods were analyzed: 96, 144, 192, 216, 240, 264, and 288 hours. A single flask of cells was analyzed at each prescribed time period. The media was exchanged in all remaining vials following three days (72 hours), five days (120 hours), seven days (168 hours), and daily thereafter. The periods were selected so that measurement would take place 24 hours after the media was exchanged. Factor analysis was carried out using Eve Technologies Rat Cytokine Array/Chemokine Array 27-Plex Panel, TGF-Beta 3-Plex Cytokine Array and Rat Bone 1-Plex Array. The specific factors compared in Table 1 include interleukin-10 (IL-10), interferon gamma-induced protein 10 (IP-10), CXCL1 (GRO/KC), vascular endothelial growth factor (VEGF), osteoprotegerin (OPG), transforming growth factor beta 1 (TGF-β1), transforming growth factor beta 2 (TGF-β2), transforming growth factor beta 3 (TGF-β3). It should be understood that multiplex measurements depend on a calibration curve and thus could vary to some degree, as understood by one of ordinary skill in the art.

The range of factors observed during the analyzed time periods is summarized in Table 3 below. It should be understood that concentration of factors may depend on the time period that the cells are cultured and number of cells in the flask.

TABLE 3

Comparison of factor concentrations for rb-MSCs and hb-MSCs in pg/ml

| Factor | rb-MSC | hb-MSC |
|---|---|---|
| IL-10 | 0 to 12 | 12 to 38 |
| IP-10 | 7 to 26 | 18 to 120 |
| GRO/KC | 14 to 100 | 460 to 5600 |
| VEGF | 300 to 2400 | 760 to 15800 |
| OPG | 540 to 3200 | 0 to 90 |
| TGF-β1 | 550 to 2600 | 67 to 2000 |
| TGF-β2 | 520 to 3200 | 170 to 2900 |
| TGF-β3 | 100 to 610 | 0 to 40 |

Comparative Analysis of Rb-MSC and Hb-MSC Lines

There are a number of ways to distinguish the hb-MSC line from the rb-MSC line. One way to distinguish two lines is by measuring the pH of the culture media during cell growth. Example 7 describes measuring the pH of culture media (RPMI-1640) conditioned by the rb-MSC and hb-MSC lines over a period of 288 hours. Prior to culture, the pH of RPMI-1640 was measured as approximately 7.01. As expected, the prescribed amount of supplemental $CO_2$ for RPMI-1640 (i.e. 5%) effectively buffered the pH of the control RPMI-1640 to 7.2 for the entire duration of the experiment. The pH of the rb-MSC culture remained between approximately 7.08 and 7.2 throughout the duration of the entire experiment. For hb-MSCs, however, the pH decreased from approximately 7.2 at 24 hours to a pH of approximately 6.6 over the course of the following 216 hours and remained at a pH approximately 6.6 for the duration of the experiment. Following 150 hours in culture, the pH of the culture medium decreases to below 7.0 within 24 hours of media exchange. Similarly, following 150 hours in culture, the pH of the culture medium decreases by at least 0.4 units from the pH of RPMI-1640 within 24 hours of media exchange. The difference in the pH of media conditioned by the rb-MSC and hb-MSC lines demonstrates that the two lines are different.

Another method to distinguish the hb-MSC line from the rb-MSC line is by measuring the production of lactate by the cells in the medium, as described in Example 7. FIG. 7 shows that hb-MSCs produce lactate resulting in a concentration that exceeds that produced by rb-MSCs. Following about 96 hours in culture, the hb-MSCs produce at least 4 mM of lactate within 24 hours of media exchange, and can produce as much as 12.4 mM of lactate within 24 hours of media exchange. By contrast, the concentration of lactate produced by rb-MSCs never exceeds 3 mM within 24 hours of media exchange. The difference in the lactate concentration in media conditioned by the rb-MSC and hb-MSC lines demonstrates that the two lines are different.

Another method to distinguish the hb-MSC line from the rb-MSC line is by evaluating the media conditioned by each line. For purposes of this comparison, the media was collected as described in Example 8. The results of the factor measurements are summarized in Table 3 above. The difference in the concentrations of the factors in media conditioned by rb-MSCs and media conditioned by hb-MSCs demonstrates that the two lines are different.

In total, the characterization methods described above lead to the conclusion that the hb-MSC line is different from the rb-MSC line.

While the present invention has been particularly shown and described with reference to exemplary embodiments thereof, it will be understood by those of ordinary skill in the art that various changes in form and details may be made therein without departing from the spirit and scope of the present invention as defined by the following claims, and their equivalents.

What is claimed is:

1. A composition comprising:
   (a) an artificial culture medium conditioned by a population of non-fetal mesenchymal stem cells seeded at $0.7 \times 10^6$ cells per 75 cm² surface area, and
   (b) some or all of said population of non-fetal mesenchymal stem cells,
   wherein the conditioned medium contains at least 760 pg/ml of vascular endothelial growth factor (VEGF) and at least 150 pg/ml of growth-regulated oncogene/keratinocyte chemoattractant (GRO/KC).

2. The composition of claim 1, wherein the conditioned medium contains at least 8,000 pg/ml of VEGF.

3. The composition of claim 1, wherein the conditioned medium further contains at least two of interleukin-10 (IL-10), interferon gamma-induced protein 10 (IP-10), transforming growth factor beta 1 (TGF-β1), and transforming growth factor beta 2 (TGF-β2).

4. The composition of claim 1, wherein the conditioned medium contains at least 4000 pg/ml of VEGF; at least 1000 pg/ml of GRO/KC; at least 750 pg/ml of TGF-β1; and at least 250 pg/ml of TGF-β2.

5. The composition of claim 1, wherein the mesenchymal stem cells used to condition the culture medium of (a) are characterized by positive expression of CD29 and CD44 markers and negative expression of CD11b and CD45 markers.

6. The composition of claim 1, wherein at least 90% of the mesenchymal stem cells used to condition the culture medium of (a) exhibit a karyotype of 2n=42.

7. The composition of claim 1, wherein the conditioned medium is conditioned by the mesenchymal stem cells in (a) having at least one of the following characteristics when $0.7 \times 10^6$ of the cells are seeded into a 75 cm² flask and cultured for at least 96 hours: (a) the cells produce at least 4.5 mM of lactate within 24 hours of media exchange; (b) the cells produce at least 150 pg/ml of GRO/KC within 24 hours of media exchange; (c) the cells produce less than 250 pg/ml of OPG following 24 hours after media exchange; and (d) the cells produce less than 80 pg/ml of TGF-β3 following 24 hours after media exchange.

8. The composition of claim 7, wherein the mesenchymal stem cells used to condition the culture medium of (a) have at least two of said characteristics.

9. The composition of claim 1, wherein the condition medium is conditioned in (a) by stem cells of a mesenchymal stem cell line deposited with Russian National Collection of Industrial Microorganisms (VKPM) as accession Number H-154.

10. The composition of claim 1, further comprising at least one of a carrier, a preservative, and a surfactant.

11. The composition of claim 1, wherein the conditioned medium is processed to remove the population of non-fetal mesenchymal stem cells from the conditioned medium.

12. The composition of claim 1, further comprising a second population of non-fetal mesenchymal stem cells.

13. The composition of claim 1, wherein the mesenchymal stem cells in (a) are derived from bone marrow, and wherein the conditioned medium contains less than 50 pg/ml of osteoprotegerin (OPG).

14. The composition of claim 1, wherein the composition contains less than 250 pg/ml of OPG or less than 80 pg/ml of TGF-β3.

15. The composition of claim 1, further comprising a preservative and a surfactant, wherein the preservative is one or more of thimerosol, cresols, formalin, benzalkonium chloride or benzyl alcohol, and wherein the surfactant is triton X-100.

16. A composition comprising, a mixture of factors comprising VEGF, GRO/KC, TGF-β1, and TGF-β2, wherein VEGF is present at a concentration of at least 760 pg/ml and GRO/KC is present at a concentration of at least 150 pg/ml, and a carrier.

17. The composition of claim 16, wherein VEGF is present at a concentration of at least 8,000 pg/ml.

18. The composition of claim 16, wherein the factors are present at concentrations of: at least 4000 pg/ml VEGF; at least 1000 pg/ml GRO/KC; at least 750 pg/ml TGF-β1; and at least 250 pg/ml TGF-β2.

19. The composition of claim 1, wherein the conditioned medium is a combination of culture media conditioned by the mesenchymal stem cells of (a) for at least two different time periods.

20. The composition of claim 16, wherein the mixture further comprises IL-10 and IP-10.

21. The composition of claim 16, further comprising a preservative and a surfactant.

22. The composition of claim 16, wherein the carrier is selected from the group consisting of a liquid, a cream, an aerosol, a lotion, an ointment, and a hydrogel.

23. The composition of claim 21, wherein the preservative is one or more of thimerosol, cresols, formalin, benzalkonium chloride or benzyl alcohol, and wherein the surfactant is triton X-100.

24. A composition comprising:
(a) an artificial culture medium conditioned by a population of non-fetal mesenchymal stem cells, and
(b) some or all of the population of said non-fetal mesenchymal stem cells,
wherein the conditioned medium contains transforming growth factor-β1 (TGF-β1), transforming growth factor-β2 (TGF-β2), at least 760 pg/ml of vascular endothelial growth factor (VEGF) and at least 150 pg/ml of growth-regulated oncogene/keratinocyte chemoattractant (GRO/KC).

25. The composition of claim 24, wherein the composition contains at least 8000 pg/ml VEGF.

26. The composition of claim 24, wherein the composition contains at least 4000 pg/ml VEGF; at least 1000 pg/ml GRO/KC; at least 750 pg/ml TGF-β1; and at least 250 pg/ml TGF-β2.

27. The composition of claim 24, wherein the composition further comprises IL-10 and IP-10.

28. The composition of claim 24, wherein the composition further comprises at least one of a carrier, a preservative, and a surfactant.

29. A method for providing a therapeutic application to a subject, said method comprising administering a therapeutically effective amount of the composition of claim 16 to a subject in need thereof.

30. The method of claim 29 wherein the therapeutic application is one or more applications selected from the group consisting of burn treatment, skin care, angiogenesis, vasculogenesis, healing of organs or tissue, tissue inflammation, bacterial infections, wound applications, diabetes, pharmaceutical and ophthalmological applications, scar reductions, stimulating hair growth, in immunotherapy applications and for immunocorrection therapy, skin, bone marrow, or organ transplants, and the treatment of organs or tissue.

31. The method of claim 29, wherein the composition is administered by injecting, implanting, or topically applying the composition.

* * * * *

SEQUENCE LISTING

<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: Forward PCR primer for human COX1

<400> SEQUENCE: 1
tagacatcgt actacacgac acg                                              23

<210> SEQ ID NO 2
<211> LENGTH: 20
<212> TYPE: DNA
<213> ORGANISM: Artificial Sequence
<220> FEATURE:
<223> OTHER INFORMATION: Reverse PCR primer for human COX1

<400> SEQUENCE: 2
tccaggttta tggagggttc                                                  20

<210> SEQ ID NO 3
<211> LENGTH: 22
<212> TYPE: DNA
<213> ORGANISM: Artificial Sequence
<220> FEATURE:
<223> OTHER INFORMATION: Forward PCR primer for rat COX1

<400> SEQUENCE: 3
cggccaccca gaagtgtaca tc                                               22

<210> SEQ ID NO 4
<211> LENGTH: 22
<212> TYPE: DNA
<213> ORGANISM: Artificial Sequence
<220> FEATURE:
<223> OTHER INFORMATION: Reverse PCR primer for rat COX1

<400> SEQUENCE: 4
ggctcgggtg tctacatcta gg                                               22

<210> SEQ ID NO 5
<211> LENGTH: 20
<212> TYPE: DNA
<213> ORGANISM: Artificial Sequence
<220> FEATURE:
<223> OTHER INFORMATION: Forward PCR primer for human VN1R1

<400> SEQUENCE: 5
tggtctgggc cagtggctcc                                                  20

<210> SEQ ID NO 6
<211> LENGTH: 25
<212> TYPE: DNA
<213> ORGANISM: Artificial Sequence
<220> FEATURE:
<223> OTHER INFORMATION: Reverse PCR primer for human VN1R1

<400> SEQUENCE: 6
gagtgttttc cttgtcctgc aggca                                            25

<210> SEQ ID NO 7
<211> LENGTH: 25
<212> TYPE: DNA
<213> ORGANISM: Artificial Sequence

```
<220> FEATURE:
<223> OTHER INFORMATION: Forward PCR primer for rat VN1R1

<400> SEQUENCE: 7
agaagagtta ctggcccaag ggaca                                          25

<210> SEQ ID NO 8
<211> LENGTH: 20
<212> TYPE: DNA
<213> ORGANISM: Artificial Sequence
<220> FEATURE:
<223> OTHER INFORMATION: Reverse PCR primer for rat VN1R1

<400> SEQUENCE: 8
ggggctgaac gctgggaagc                                                20
```